United States Patent
Fortin

(10) Patent No.: US 10,098,554 B2
(45) Date of Patent: Oct. 16, 2018

(54) METHOD AND DEVICE FOR CONTINUOUS, NON-INVASIVE DETERMINATION OF BLOOD PRESSURE

(71) Applicant: CNSYSTEMS MEDIZINTECHNIK AG, Graz (AT)

(72) Inventor: Jurgen Fortin, Graz (AT)

(73) Assignee: CNSYSTEMS MEDIZINTECHNIK AG, Graz (AT)

( * ) Notice: Subject to any disclaimer, the term of this patent is extended or adjusted under 35 U.S.C. 154(b) by 487 days.

(21) Appl. No.: 14/404,095

(22) PCT Filed: May 16, 2013

(86) PCT No.: PCT/EP2013/060113
§ 371 (c)(1),
(2) Date: Nov. 26, 2014

(87) PCT Pub. No.: WO2013/178475
PCT Pub. Date: Dec. 5, 2013

(65) Prior Publication Data
US 2015/0201852 A1    Jul. 23, 2015

(30) Foreign Application Priority Data
May 31, 2012 (AT) .................................. 50211/2012

(51) Int. Cl.
*A61B 5/0225* (2006.01)
*A61B 5/021* (2006.01)
*A61B 5/00* (2006.01)

(52) U.S. Cl.
CPC ...... *A61B 5/02255* (2013.01); *A61B 5/02116* (2013.01); *A61B 5/6826* (2013.01); *A61B 5/6843* (2013.01); *A61B 5/6838* (2013.01)

(58) Field of Classification Search
CPC ............ A61B 5/02116; A61B 5/02255; A61B 5/6826; A61B 5/6838; A61B 5/6843
See application file for complete search history.

(56) References Cited

U.S. PATENT DOCUMENTS

| 4,510,940 A | 4/1985 | Wesseling |
| 4,539,997 A | 9/1985 | Wesseling et al. |

(Continued)

FOREIGN PATENT DOCUMENTS

| EP | 0537383 | 4/1993 |
| EP | 2319408 | 5/2011 |

(Continued)

OTHER PUBLICATIONS

International Search Report for Int. App. No. PCT/EP2013/060113, completed Aug. 14, 2013.

(Continued)

*Primary Examiner* — Katherine Fernandez
(74) *Attorney, Agent, or Firm* — McDonnell Boehnen Hulbert & Berghoff LLP

(57) ABSTRACT

The invention relates to a method and a device for continuously determining blood pressure in a non-invasive manner using a photoplethysmographic system which has at least one light source and at least one light detector that is arranged with a mount on a body part containing an artery. According to the invention, a device is provided with which the contact pressure of the mount on the body part can be adjusted and/or changed depending on the mean blood pressure.

9 Claims, 9 Drawing Sheets

(56) References Cited

U.S. PATENT DOCUMENTS

| | | | |
|---|---|---|---|
| 4,597,393 A | 7/1986 | Yamakoshi et al. | |
| 2002/0173709 A1 | 11/2002 | Fine et al. | |
| 2005/0148885 A1 | 7/2005 | Tweed et al. | |
| 2006/0195034 A1 | 8/2006 | Skrabal et al. | |
| 2007/0032729 A1 | 2/2007 | Fortin et al. | |
| 2009/0326395 A1* | 12/2009 | Watson | A61B 5/021 600/500 |
| 2010/0298678 A1 | 11/2010 | Klomhaus | |

FOREIGN PATENT DOCUMENTS

| | | |
|---|---|---|
| WO | 00/59369 | 10/2000 |
| WO | 2004/086963 | 10/2004 |
| WO | 2005/037097 | 4/2005 |
| WO | 2011/051819 | 5/2011 |
| WO | 2011/051822 | 5/2011 |

OTHER PUBLICATIONS

Peñáz J: Photoelectric Measurement of blood pressure, volume and flow in the finger. Digest of the 10th international conference on medical and biological engineering—Dresden (1973).

* cited by examiner

METHOD AND DEVICE FOR CONTINUOUS, NON-INVASIVE DETERMINATION OF BLOOD PRESSURE

CROSS REFERENCE TO RELATED APPLICATIONS

The present application is a U.S. National Phase Application pursuant to 35 U.S.C. § 371 of International Application No. PCT/EP2013/060113 filed May 16, 2013, which claims priority to Austrian Patent Application No. A 50211/2012 filed May 31, 2012. The entire disclosure contents of these applications are herewith incorporated by reference into the present application.

BACKGROUND

The invention relates to a method and an apparatus for the continuous, non-invasive determination of blood pressure by means of a photoplethysmographic system comprising at least one light source and at least one light detector, which are attached to a body part containing an artery.

To this day the continuous and non-invasive measuring of blood pressure presents a serious challenge to measuring technology. At the moment the so-called "Vascular Unloading Technique" is gaining more and more acceptance, which is based on a publication by Penaz (Digest of the $10^{th}$ International Conference on Medical and Biological Engineering, Dresden 1973), in which light is passed through a finger and the registered flow is held constant by means of a servo-control device.

The photoplethysmographic method according to Penaz, also known as "Vascular Unloading Technique" or as "Volume Clamp Method" in some publications, has been further improved. EP 0 537 383 A1 (TNO) discloses for instance an inflatable finger cuff for non-invasive, continuous blood pressure monitoring. The inflatable cylindrical space is pneumatically connected to a fluid source. An infrared light source and a detector are placed on either side of the finger within the rigid cylinder. A valve is provided for filling the cylinder with gas. Electrical leads for the infrared light source and the detector are introduced into the cylinder. U.S. Pat. No. 4,510,940 A (Wesseling) and U.S. Pat. No. 4,539,997 A (Wesseling) show devices for the continuous, non-invasive measuring of blood pressure. A fluid-filled cuff, a light source, a light detector, a differential pressure amplifier are provided. U.S. Pat. No. 4,597,393 (Yamakoshi) also shows a variant of the Penaz principle.

WO 00/59369 A2 describes improvements of the valve control and of the pressure generating system, and various types of pressure cuffs (e.g. double cuff) for different limbs. WO 04/086963 A2 contains a description of how a double cuff can be used in such a way that in one cuff blood pressure is measured according to the Penaz principle, while the other cuff carries out optimized control of the set point (SP). WO 05/037097 A1 describes an improved control system for the vascular unloading technique, in which inner control loops present a quasi-optimized situation to the next outer control loops.

WO 2011/051822 A1 describes how signal quality of the vascular unloading technique can be improved, such that subsequently a method of pulse-shape analysis may be used for obtaining further parameters. WO 2011/051819 A1 describes an improved, exclusively digital method and device for the vascular unloading technique.

The method of Penaz has been further developed and enhanced in numerous patents and publications without however eliminating a fundamental disadvantage of the method: in order to obtain the blood pressure signal a sensor must be attached to the finger, whose contact pressure must be adapted in real time to the arterial blood pressure in the finger. Implementing this kind of fast pressure adjustment requires considerable effort and cost. All disclosures up to now use a cuff to this end, which is connected to a pump and a complex valve or valve system. The inner pressure of the cuff acting on the finger is controlled in such a way that it equals the arterial blood pressure. This is the case when the photoplethysmographic signal measured at the same time is constant.

Ideally the cuff pressure must be able to undergo changes which are as rapid as those occurring in actual arterial blood pressure, i.e. it must cope with frequencies of change in a range up to 20 Hz. This imposes costly requirements on valve or valve system, pump and cuff, which one would like to avoid. The present invention intends to substantially reduce these costs.

SUMMARY

It is an object of the present invention to provide a method and apparatus for the continuous, non-invasive determination of blood pressure or the blood pressure signal $p_{BP}(t)$ [mmHg], which is simple to realize and easy to use. It would be desirable to have only a photoplethysmographic system without any costly pressure system. A photoplethysmographic system essentially consists of a light source (preferably LED type) and a light detector (e.g. a photodiode) and is well known from pulse oximetry. The signal obtained $v(t)$ (dimensionless, as long as it not calibrated for instance relative to liter) represents a measure for the volume in the finger (plethysmography)—its pulsations correspond to the volume of arterial blood. The DC component of the signal is determined by the thickness of the finger and its tissue components, the laminary flow of venous blood, and other factors such as ambient light. The photoplethysmographic signal $v(t)$ also comprises varying components, which are mostly determined by the vascular wall of the finger artery. The finger arteries are blood vessels of a kind that are constricted (vaso-constriction) or dilated (vaso-dilatation) by the autonomic nervous system (vegetative control). These vasomotoric changes will alter the photoplethysmographic signal to such an extent that it is unsuitable for direct use in blood pressure measurement.

The object according to the invention is achieved by proposing that the contact pressure $p(t)$ of the photoplethysmographic system be varied depending on the mean blood pressure, or rather be adapted to the mean blood pressure.

An apparatus according to the invention—based on a photoplethysmographic system with at least one light source and at least one light detector, which are attached by a mounting element to a body part containing an artery—is characteristically provided with a mechanism by which the contact pressure $p(t)$ exerted by the mounting element on the body part, may be varied depending on the mean blood pressure.

The essential point is that the contact pressure $p(t)$ [mmHg], or rather, the contact force of the mounting element, i.e. the contact force of the plethysmographic system, is varied in such a way that it corresponds to the mean blood pressure (mean arterial blood pressure MABP). The MABP changes relatively slowly as compared to the real pulsatile intra-arterial blood pressure $p_{BP}(t)$. While for following the arterial blood pressure $p_{BP}(t)$ a pressure or cuff system is needed which is able to handle pressure signals with frequencies of up to 20 Hz, a device for following the variations of the mean blood pressure MABP is only expected to handle frequencies far below those of pulsations. Such a device may preferably be realised using simple mechanical systems, such as step motors, linear actuators or the like, or simple pneumatic systems (finger cuffs) without complicated valve systems.

For adaptive control it will be necessary first of all to find a suitable starting point. To this end the fact is utilised that the pulsations of the plethysmographic signal v(t) are largest when the contact pressure p(t) equals the mean blood pressure MABP. The contact pressure p(t) is therefore initially varied until the pulsations reach a maximum (search phase). Subsequently adaptive following of the contact pressure p(t) is activated (measuring phase). The initial plethysmographic signal $v_0$ obtained at this point is stored for use in subsequent control of pressure following.

Control of the pressure following activity is based on the fact that the plethysmographic signal v(t) is made suitable for adjusting the contact pressure by passing it through a low-pass filter. The filtered "low frequency LF" signal $v_{LF}(t)$ is compared with the initial plethysmographic signal $v_0$ and contact pressure p(t) is varied until the filtered signal $v_{LF}(t)$ again corresponds to the initial signal $v_0$.

To compensate vasomotoric changes one utilises the fact that for mean blood pressure the negative, or systolic, half-wave of v(t) is of equal size as the positive, or diastolic, half-wave. If this is not the case the set point and thus the pressure is varied until both half-waves again have the same amplitude.

The plethysmographic signal v(t) thus obtained does not yet correspond to the true blood pressure signal $p_{BP}(t)$, since the absolute values of blood pressure cannot be determined in this way. For this reason blood pressure is determined by another intermittent standard method, such as oscillometrically at the upper arm, and a transfer function is computed for the photoplethysmographic signal v(t). Application of the transfer function to the plethysmographic signal v(t) results in the continuous non-invasive blood pressure signal $p_{BP}(t)$.

BRIEF DESCRIPTION OF THE FIGURES

The invention will now be described in more detail, with reference to the enclosed schematic diagrams and drawings. There is shown in FIG. 1 the principle of photoplethysmography according to the state of the art.

DETAILED DESCRIPTION

Figure 1:
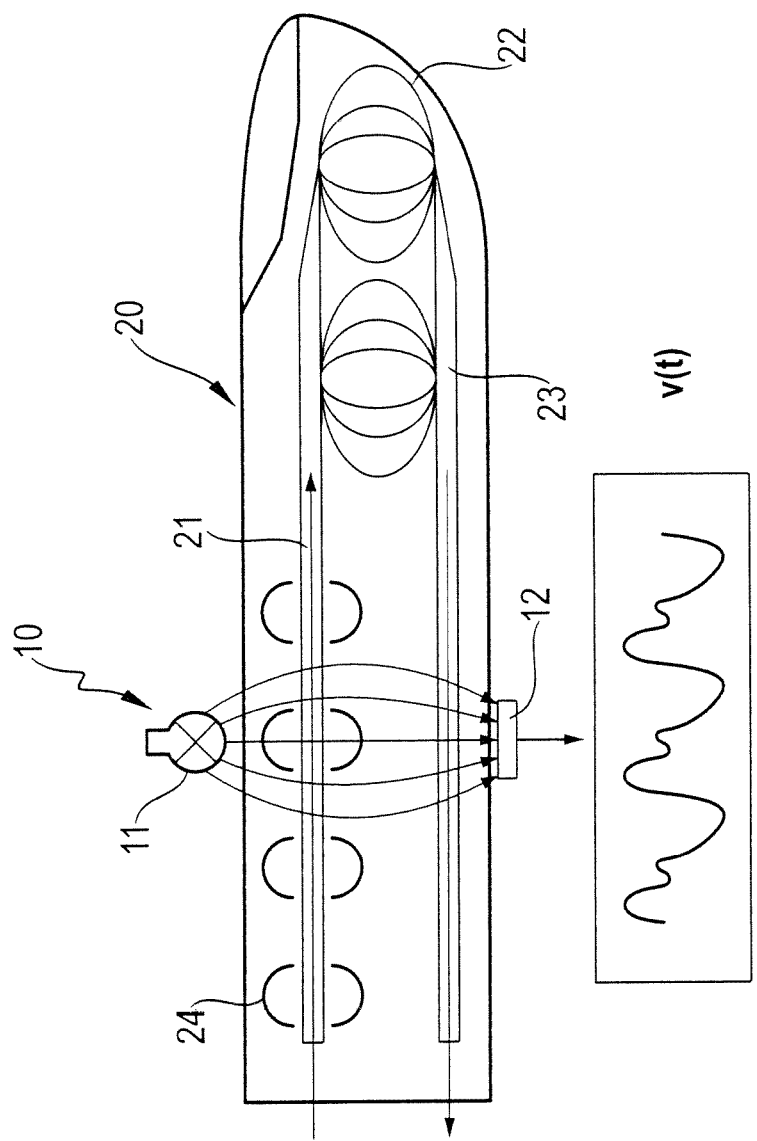

FIG. 1 illustrates the principle of photoplethysmography. The schematically shown apparatus essentially consists of a photoplethysmographic system 10 with at least one light source 11 (e.g. a LED) and at least one light detector 12, which produces a photoplethysmographic signal v(t). Light is shone through a body part, e.g. a finger 20, and is primarily absorbed by arterial blood in the artery 21. Capillary vessels are referred to as 22, the finger vein is 23. Pulsatile pressure changes are indicated by bulges 24 of the artery 21. On the other side of the finger 20 residual light is received by the light detector 12 and converted into an electric signal v(t). The signal invertedly mirrors the arterial blood volume curve and changes in the diameter of the finger artery, respectively.

Figure 2:
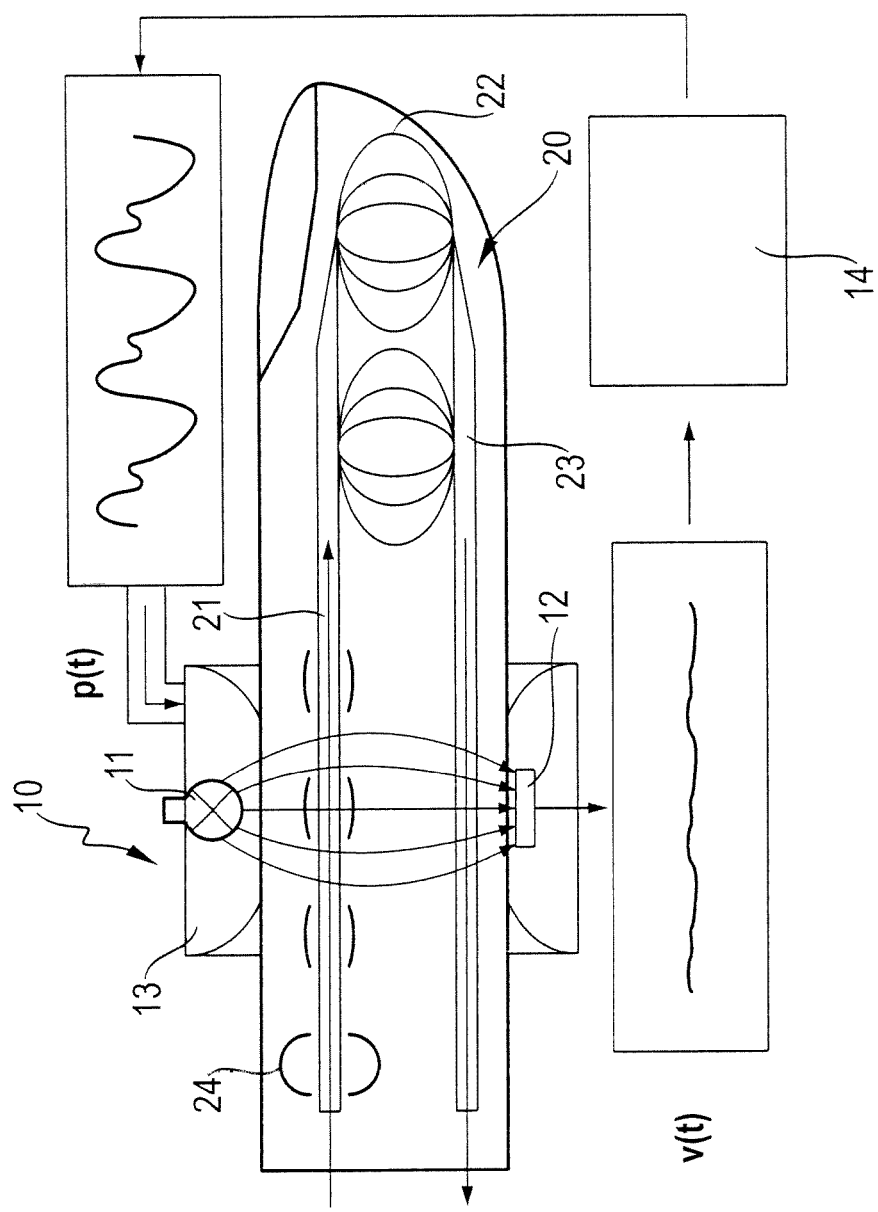
FIG. 2 the principle of the "Vascular Unloading Technique" according to the state of the art.

FIG. 2 describes the principle of the "Vascular Unloading Technique". The vascular unloading technique was developed in order to be able to determine blood pressure non-invasively and continuously. The vessel wall of the finger artery is kept free of tension by controlling the pressure of the surrounding cuff or mounting element 13 fast enough, such that the cuff pressure precisely compensates the arterial pressure in the artery 21 of the finger 20. This is the case when the resulting photoplethysmographic signal v(t) is kept constant. This principle requires a rapidly responding pressure and control system 14, which preferably is realised pneumatically using a pump, a fast valve or valve system and the finger cuff 13.

Figure 3:
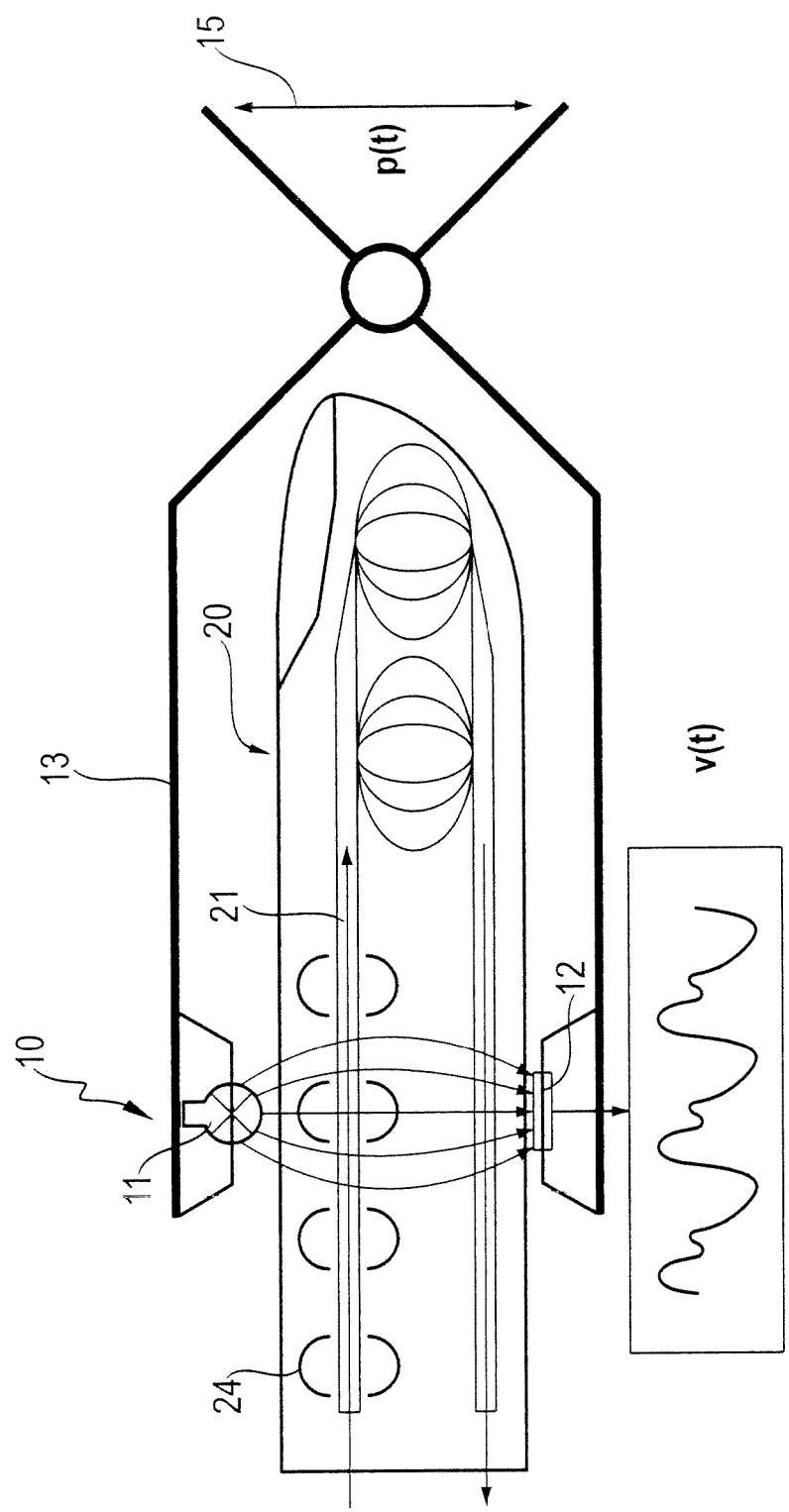
FIG. 3 the measuring principle according to the invention.

FIG. 3 shows the measuring system according to the invention. The fast pressure system of the vascular unloading technique is very complicated and thus expensive. The following considerations will show that it is not necessary to control the contact pressure p(t) of the cuff fast enough for mirroring the true pulsatile arterial pressure $p_{BP}(t)$. It is only important that the contact pressure p(t) follow the mean blood pressure MABP. The method employed for following the MABP may be far slower than the systems known from the vascular unloading technique. FIG. 3 shows a mounting element 13 (e.g. finger clips) for attaching the at least one light source 11 and the at least one light detector 12 to a body part, respectively a finger 20 containing an artery 21. According to the invention there is now provided a device 15 by which the contact pressure of the mounting element 13 on the body part can be varied depending on the mean blood pressure. Pressure following may therefore be carried out by means of a simple step motor or actuator, and a cuff with a slow valve or valve system or other suitable devices.

Figure 4:
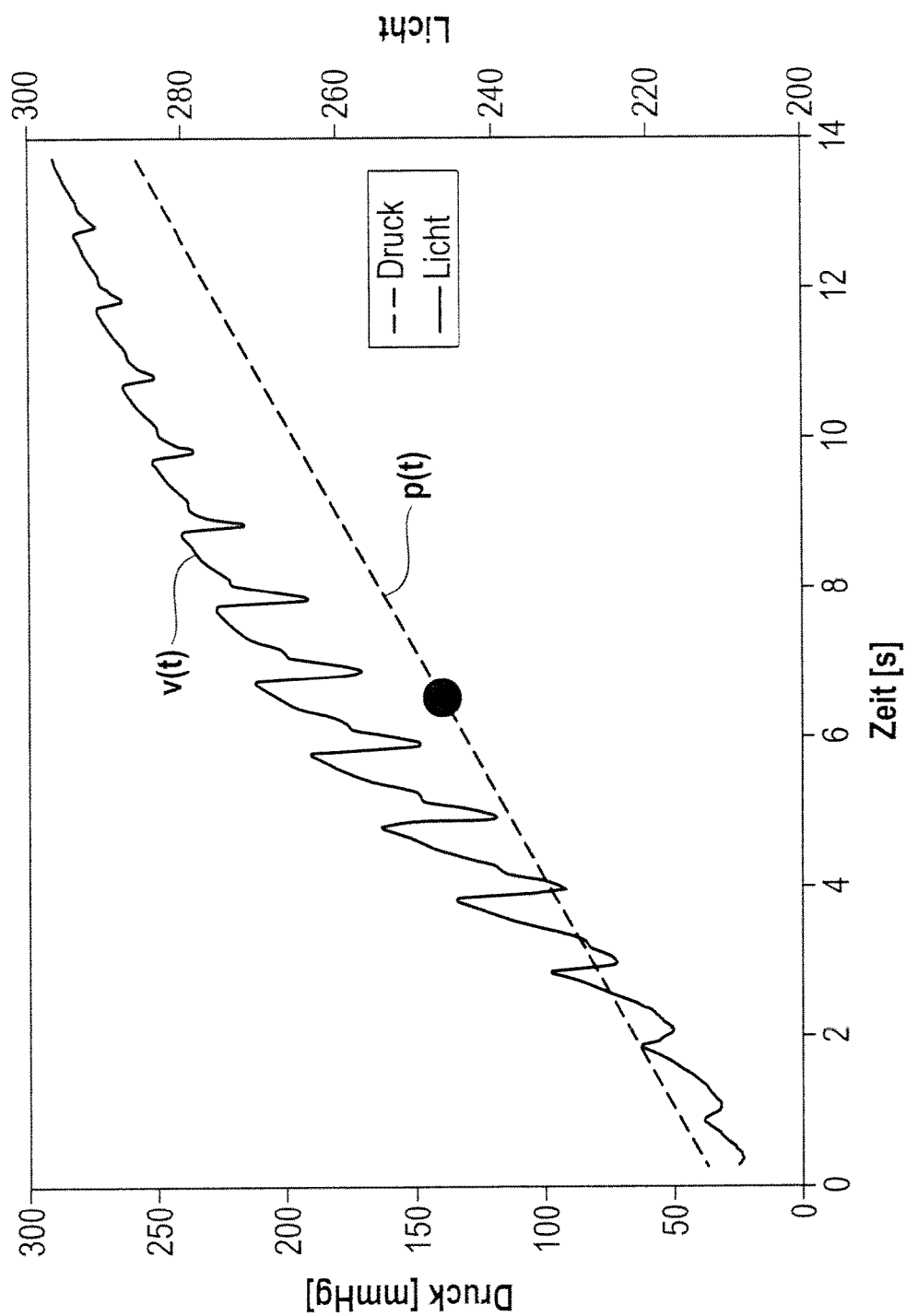
FIG. 4 a diagram of the change over time of the photoplethysmographic signal v(t) as pressure p(t) changes.

Prior to the beginning of pressure following the initial contact pressure $p_0$ of the new measuring device must be set to the mean blood pressure MABP. It has been found that the contact pressure of a photoplethysmographic system equals the mean blood pressure MABP when the signal amplitude of the photoplethysmographic signal v(t) is at its maximum. FIG. 4 shows the change in the photoplethysmographic signal v(t) with increasing pressure p(t). The black dot indicates the pressure value at which the amplitude of v(t) is greatest; this corresponds to the actual mean blood pressure MABP. This set point—initial contact pressure $p_0$ and initial plethysmo-graphic signal $v_0$—is stored by the system. The inverted behaviour of the signal v(t) should be noted here, because during the systole the finger naturally contains more blood than during the diastole. A larger volume of blood increases light absorption and thus reduces the plethysmographic signal, while during diastole the signal will increase due to lesser absorption. Due to the rise in pressure more and more blood will be squeezed from the finger, which in turn will cause an increase of the plethysmographic signal v(t) with increasing pressure p(t).

Figure 5:
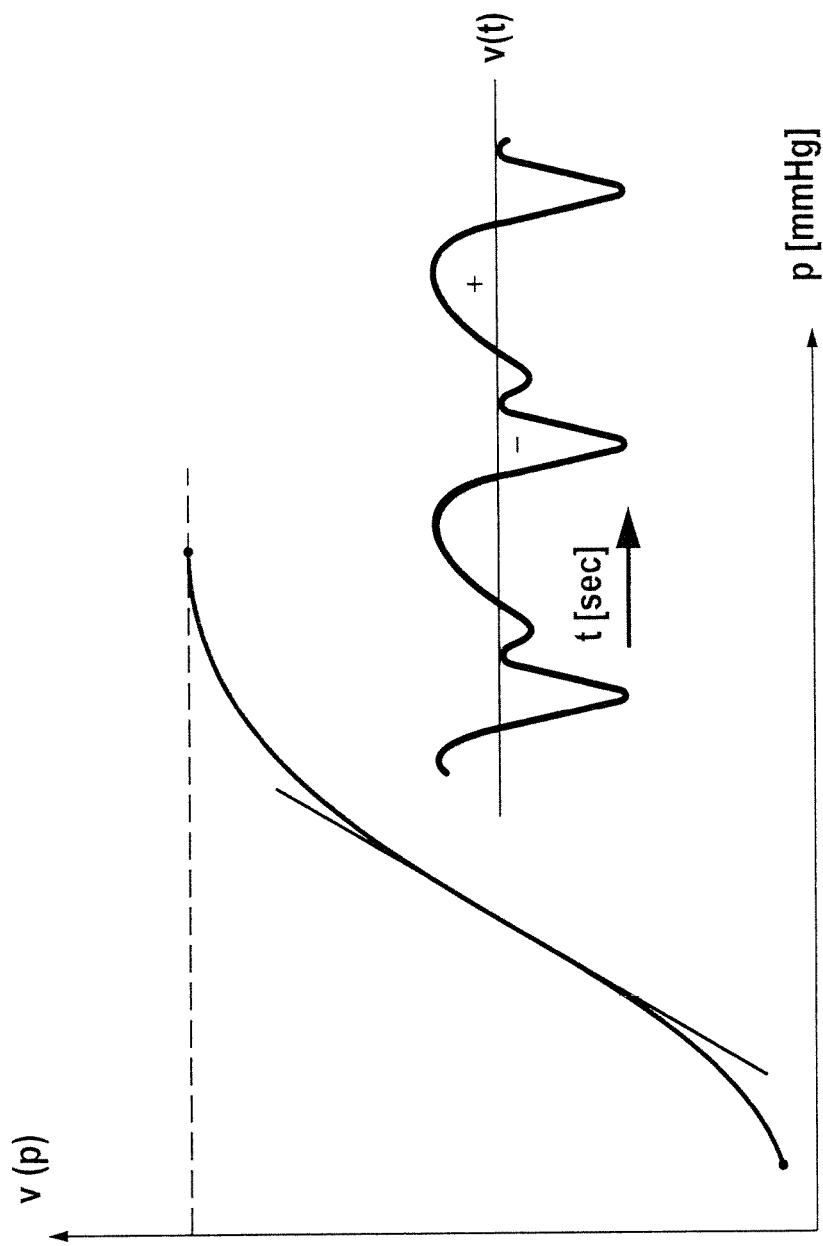
FIG. 5 a diagram of the S-shaped transfer function between contact pressure p and plethysmographic signal v(p)

FIG. 5 explains why the signal amplitude is greatest when the contact pressure exactly equals the mean blood pressure MABP. In FIG. 5 there is shown the S-shaped transfer function between contact pressure p and plethysmographic signal v(p). This S-curve arises—theoretically—when at first there are no pulsations in the artery and the plethysmographic signal is plotted against contact pressure p. Due to the actual arterial pulsations the plethysmographic signal v(t) starts oscillating around the set point set by the contact pressure.

The amplitude of the generated plethysmographic signal v(t) is determined by the slope of the S-curve. In FIG. 5 the set point is the point of inflection of the S-curve, where the maximum slope and thus the maximum plethysmographic amplitude occurs. This point corresponds to the mean blood pressure MABP.

Figure 6:
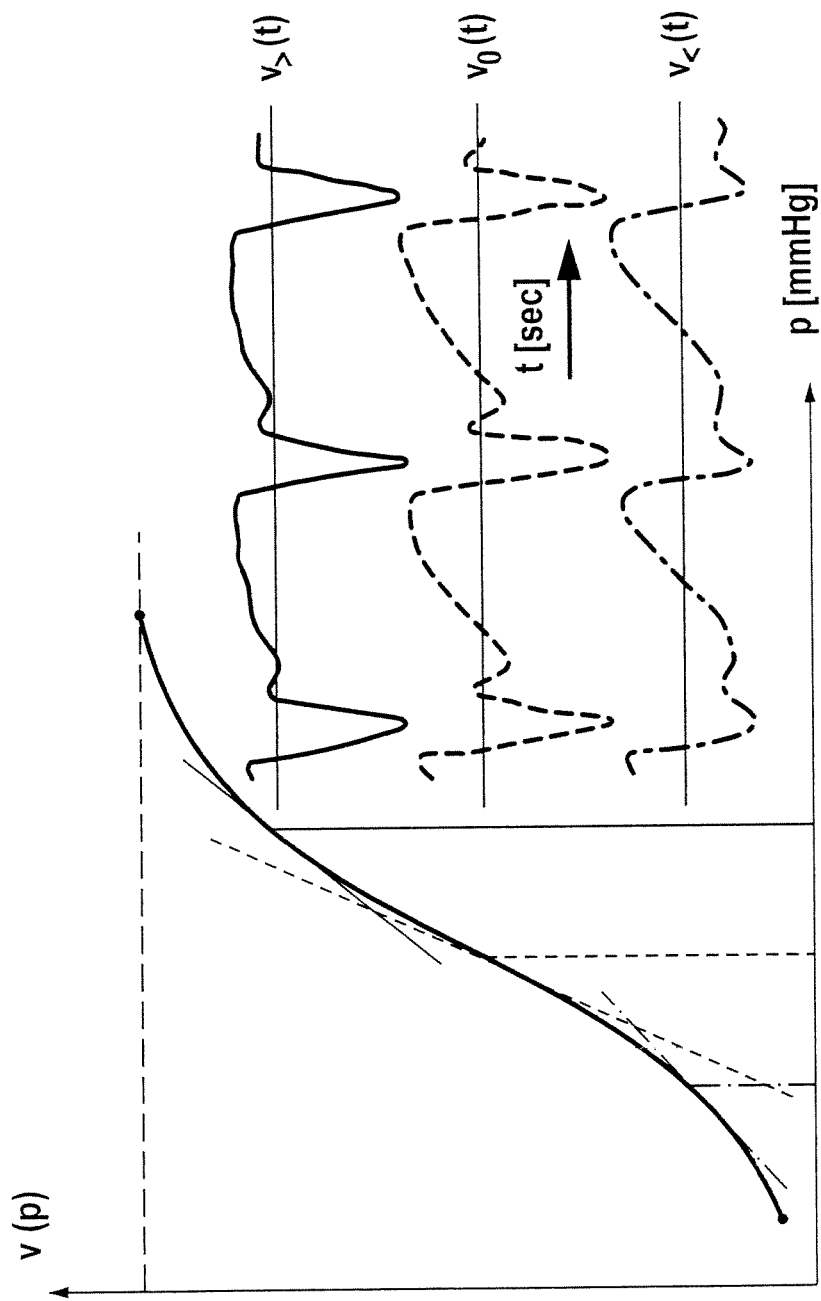
FIG. 6 various plethysmographic signals v(t) at different contact pressures p according to the S-shaped transfer function.

FIG. 6 shows how the plethysmographic signal changes when the contact pressure is less than or greater than the mean blood pressure. If the contact pressure is too low the plethysmographic signal $v_<(t)$ is generated. In contrast to $v_0(t)$, the plethysmographic signal at mean pressure, the amplitude is smaller and the shape of the signal is different. The systole appears broader, one could call the signal shape "more bulgy". In contrast to this the plethysmographic signal $v_>(t)$ at unduly high contact pressure is more "pointed" than $v_0(t)$ or $v_<(t)$. Once again, the amplitude is smaller.

Subsequent to the search for maximum amplitude, which is found at contact pressure p(t) corresponding to the mean blood pressure MABP and to the maximum slope at the inflection point of the S-curve, respectively, the system is positioned at the initial measuring point. A first idea for stabilising this set point is as following: the initial plethysmographic signal $v_0$ and the initial contact pressure $p_0$ are stored by the system as the initial set point $v_0/p_0$.

The plethysmographic signal is then filtered, causing the pulsational pressure changes to disappear (see filter $TP_{LF}$ in FIG. 9) and creating a slowly varying signal $v_{LF}(t)$, which can be followed without problems by device 15 of the invention for changing contact pressure. As a rule the cut-off frequency of the filter lies far below the frequencies of pulsatile pressure changes. The filtered signal $v_{LF}(t)$ is compared with the initial set point $v_0$ and in case of a deviation the contact pressure p(t) is adjusted until the signal $v_0$ is again attained.

Figure 7:
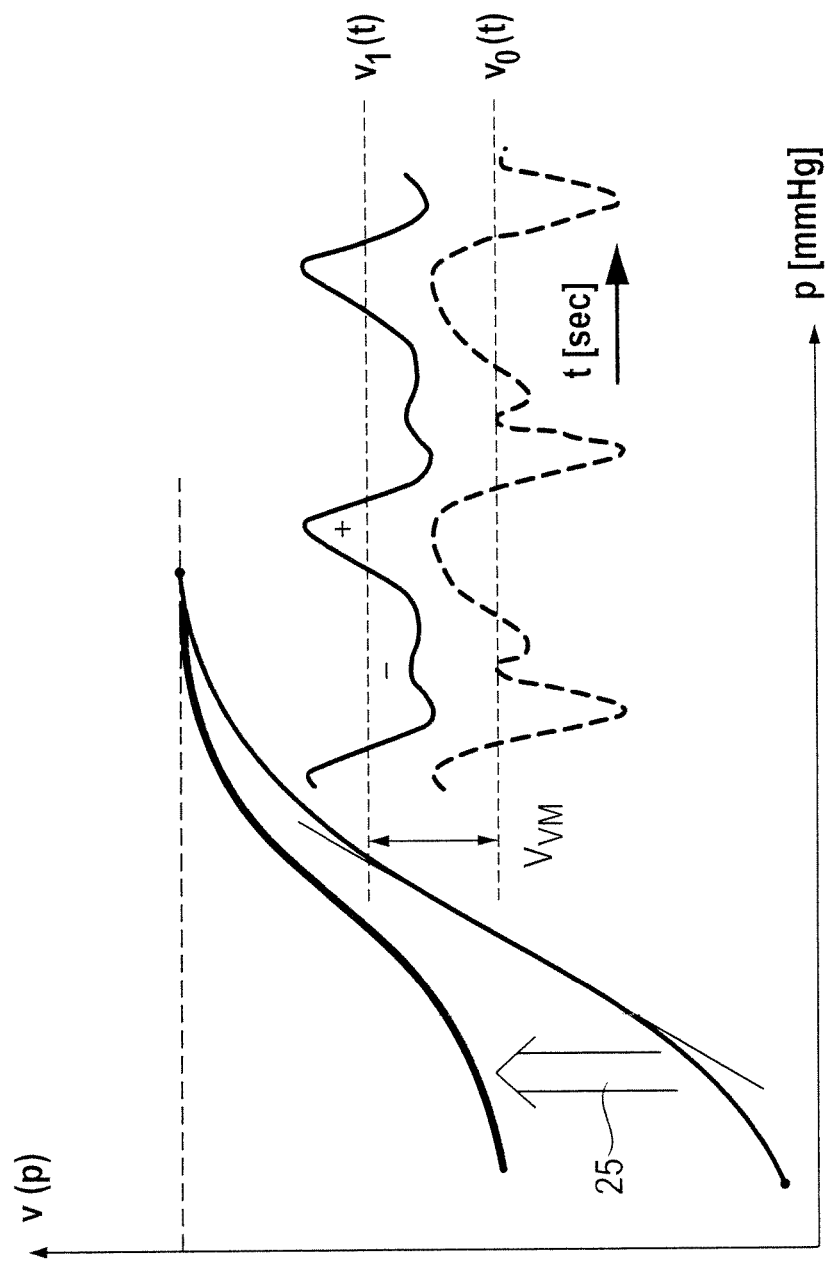
FIG. 7 changes in the S-shaped transfer function and in the plethysmographic signals under vaso-constriction.

In the diagram of the S-shaped transfer function such a pressure change corresponds to a simple shift of the S-curve to the left if pressure rises, and to the right (not shown) if pressure is reduced. Unfortunately the height of the S-curve may simultaneously grow smaller, which corresponds to a constriction of the artery (vasoconstriction as indicated by arrow 25) as can be seen in FIG. 7. If the artery becomes dilated (vasodilatation) the S-curve increases in height, in analogy to FIG. 7. These changes in the S-shaped transfer function caused by vasomotoric changes (vasoconstriction or vasodilatation) may be taken into account in the following way: first it should be noted that such changes occur very slowly, i.e. over a range of minutes. In this "very low frequency VLF" range a change in blood pressure cannot be told from a vasomotoric effect; for this reason the VLF frequency range is completely eliminated by means of a signal $v_{VLF}(t)$ also generated by low-pass filtering (see filter $TP_{VLF}$ in FIG. 9). In practice this would mean that comparison with the initial set point $v_0$ is no longer feasible, since the set point could have been shifted upwards by vasoconstriction or downwards due to vasodilatation.

Physiologically the following happens: vasoconstriction narrows the blood vessel and thus the artery contains less blood. Therefore absorption is lower and the plethysmographic signal is increased, corresponding to an upward shift of the set point (see FIG. 7). Conversely vasodilatation widens the artery and the artery contains more blood. Absorption thus increases, the plethysmographic signal decreases and the set point shifts downwards.

Figure 8:
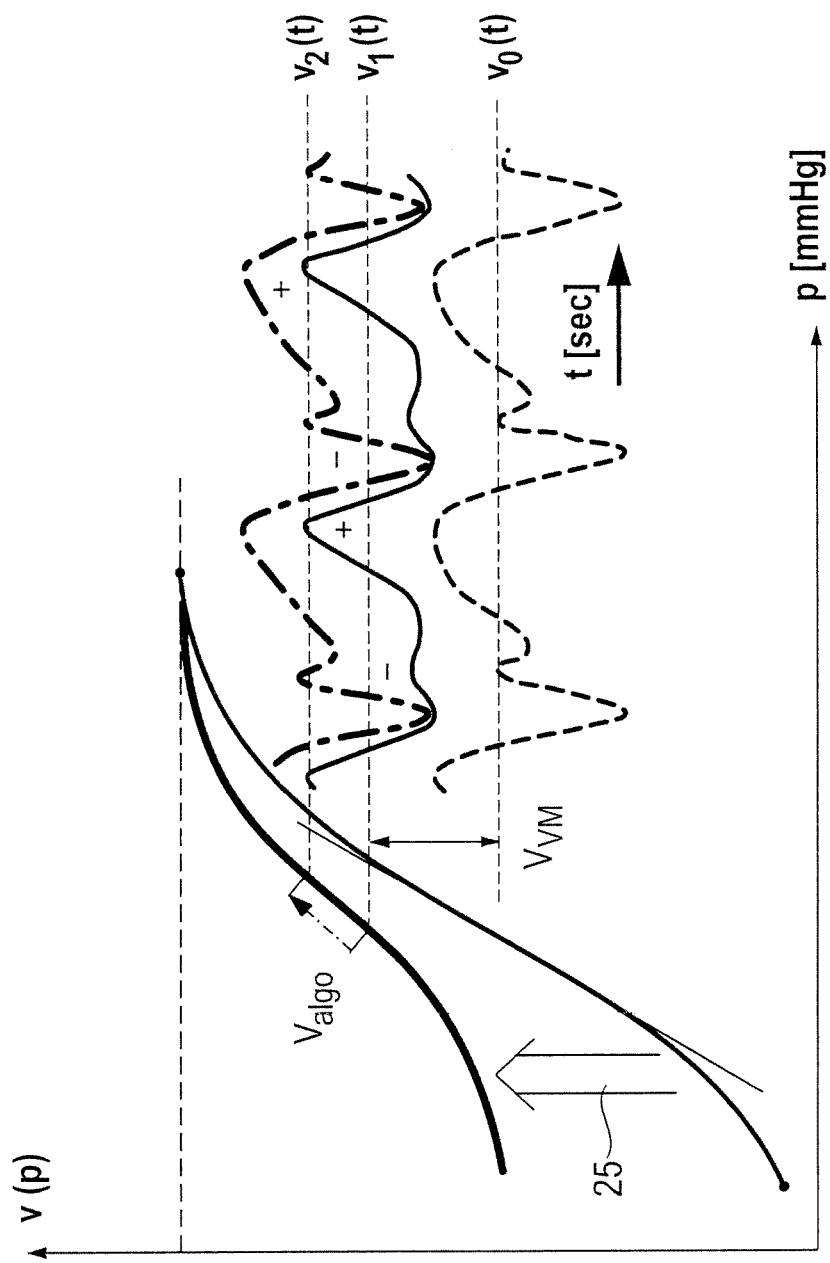
FIG. 8 pressure adjustment along the S-shaped transfer function.

From FIG. 7 we can see that there will not only occur a shift of the set point, but that the shape of the signal $v_1(t)$ will change—it becomes "more bulgy" and similar to the signal $v_<(t)$ at a contact pressure that is too low. Furthermore it can be seen that the negative half-wave (−) of $v_1(t)$ becomes greater than the positive half-wave (+). The set point $v_0$ is adjusted ($v_{algo}$) until both half-waves again are of equal size, which results in $v_2(t)$ (FIG. 8). The value of $v_0$ changed by $v_{algo}$ is now the new set point for the filtered plethysmographic signal. The contact pressure p(t) is adjusted until $v_0$ plus $v_{algo}$ again equals the filtered plethysmographic signal $v_{LF}(t)$.

Figure 9:
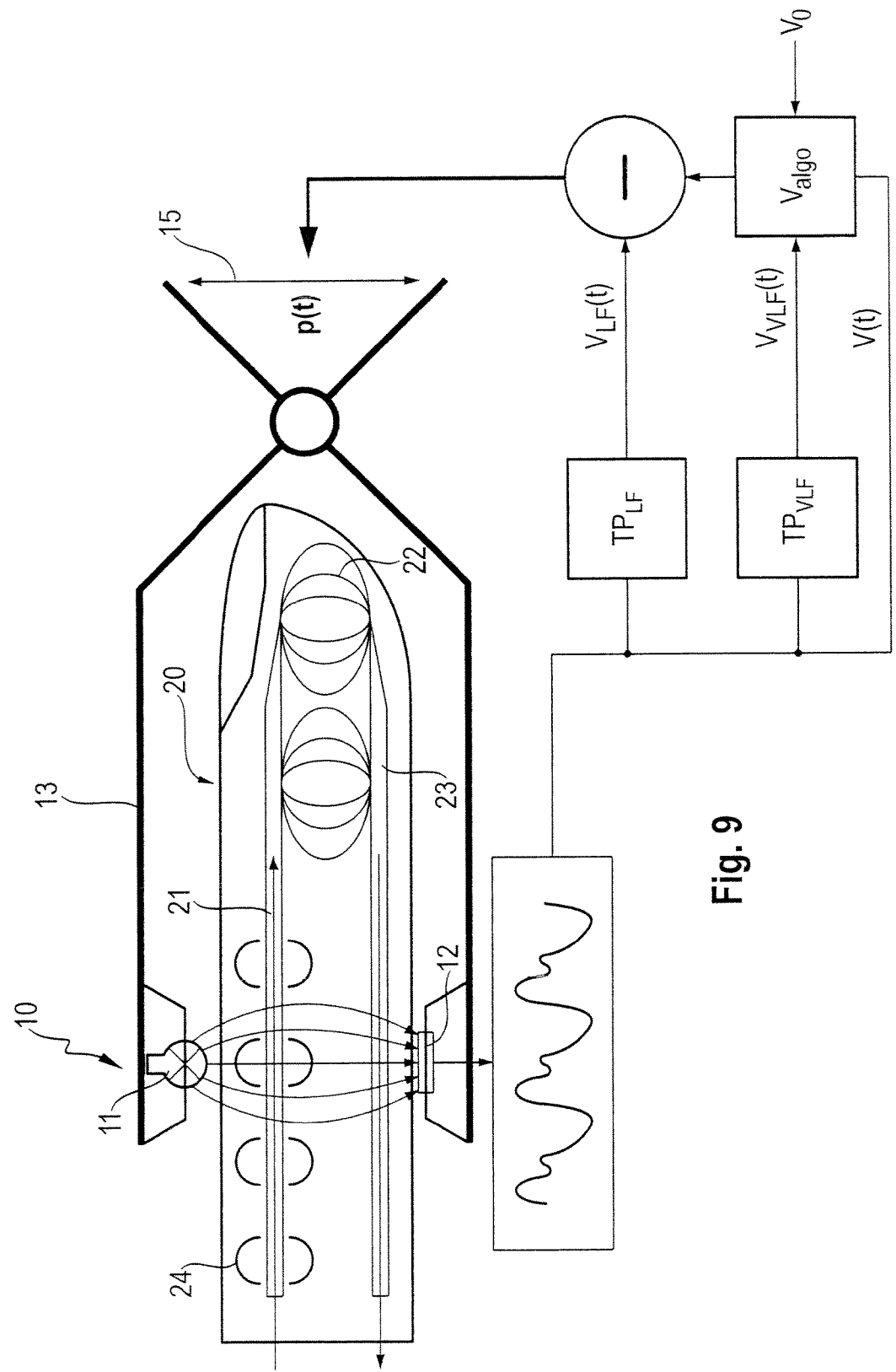
FIG. 9 a schematic presentation of the device according to the invention together with the control system.

According to FIG. 9 the control system of the apparatus of the invention preferably comprises two control paths beginning with the low-pass filters $TP_{LF}$ and $TP_{VLF}$. The first path changes the contact pressure until the filtered plethysmographic signal $v_{LF}(t)$ equals a target value. This target value is supplied by the second control path and is the sum of the initial set point $v_0$ plus an adaptive value $v_{algo}$. $v_{algo}$ is increased if the negative half-wave of the unfiltered plethysmographic signal $v(t)-v_{VLF}(t)$ is greater than the positive half-wave. If the two half-waves are equal, $v_{algo}$ remains unchanged, if the positive half-wave is greater, $v_{algo}$ decreases.

In order that the continuous blood pressure may be computed from these two signals calibration is necessary by means of a conventional blood pressure apparatus, which determines systolic sBP and diastolic dBP blood pressure. As a rule a conventional apparatus does not measure the mean blood pressure, but this can be computed using the well-known formula $$mBP = dBP + 0.33*(sBP - dBP).$$

It is also of advantage if the apparatus of the invention measures the actual contact pressure p(t) by means of a pressure sensor, which corresponds to the mean blood pressure. The blood pressure signal $p_{BP}(t)$ may then be computed as follows:

$$p_{BP}(t) = mBP + p(t) - p_0 + (sBP - dBP)/(v_{0sys} - v_{0dia})*v(t)$$

where $v_{0sys}$ and $v_{0dia}$ are the systolic and diastolic plethysmographic signals, which have been obtained during or immediately after conventional upper arm measurement.

According to a variant of the invention direct measuring of the contact pressure p(t) by means of a pressure sensor may be omitted, as the contact pressure p(t) may be determined from the position of the actuator (for instance from the position of the step motor) from the initial search phase. At the transition from search phase to measuring phase the contact pressure p(t) equals the mean blood pressure MABP. If the blood pressure of the upper arm is taken immediately afterwards the following equalities hold:

$$P(t) = MABP = mBP = p_0.$$

In the course of measurement the contact pressure may be inferred, at least relatively, from the position of the step motor.

In summary the advantages of the novel measurement method and the novel measuring apparatus lie essentially in the fact that the contact pressure p(t) and the contact force of the photoplethysmographic system are controlled to equal the mean blood pressure MABP. Thus the contact pressure varies only relatively slowly as compared with the true pulsatile blood pressure $p_{BP}(t)$ and can preferably be obtained by simple mechanical systems, such as step motors, linear actuators and simple finger cuffs without complicated valve systems. Controlled pressure following is based on the fact that first the plethysmographic signal is filtered to such a degree that it may be used for the adjustment of contact pressure, i.e. that it is slow enough for steering the sluggish mechanical system furnishing the contact pressure. The filtered signal $v_{LF}(t)$ is compared with the initial plethysmographic signal $v_0$, and the contact pressure p(t) is varied until the filtered signal $v_{LF}(t)$ again equals the initial signal $v_0$. Compensation of vasomotoric variations is also possible. The plethysmo-graphic signal arising in this case is calibrated by a known, intermittent standard method.

The invention claimed is:

1. A method for continuous, non-invasive determination of blood pressure by means of a photoplethysmographic system comprising a mounting element including at least one light source and at least one light detector, the method comprising:

obtaining an initial photoplethysmographic signal using the photoplethysmographic system;

obtaining a photoplethysmographic signal using the photoplethysmographic system;

disposing the mounting element on a body part containing an artery, and varying a contact pressure of the mounting element depending on a mean arterial blood pressure, wherein a rate of change of the contact pressure of the mounting element is smaller than that of a pulsatile blood pressure changes in the artery;

wherein the contact pressure of the mounting element is varied by a control system departing from an initial contact pressure, wherein the control system uses a low-pass filter through which the a photoplethysmographic signal is passed to generate a filtered photoplethysmographic signal, which is compared with the initial photoplethysmographic signal; and wherein, based on the comparison, the contact pressure is varied until the filtered photoplethysmographic signal again corresponds to the initial photoplethysmographic signal.

2. The method of claim 1, wherein the contact pressure of the mounting element is adapted to the mean arterial blood pressure.

3. The method of claim 1, wherein in a search phase an initial contact pressure of the mounting element is determined, at which the initial photoplethysmographic signal with maximum amplitude will arise.

4. The method of claim 3 wherein an initial set point is determined by measuring the contact pressure, where an amplitude of the photoplethysmographic signal has a highest maximum, and the initial contact pressure is stored as the initial set point.

5. The method of claim 1, wherein the control system takes into account physiological changes of the wall of an arterial vessel by means of passing the photoplethysmographic signal through a second low-pass filter.

6. The method of claim 5 wherein the control system recognizes physiological changes of the wall of the arterial vessel by comparing pulsatile signal components of the photoplethysmographic signal, the filtered photoplethysmographic signal from the second low-pass filter, and the initial photoplethysmographic signal.

7. The method of claim 1, wherein a blood pressure signal derived from the photoplethysmographic signal is calibrated by means of intermittent blood pressure monitoring.

8. The method of claim 7 wherein a mean blood pressure of an intermittent upper arm measurement, the contact pressure of the mounting element, and pulsatile photoplethysmographic signal components are used for calibration of the blood pressure signal.

9. The method of claim 1, wherein the contact pressure is obtained from a control variable used for pressure following activity.

* * * * *